(12) United States Patent
Brazdeikis et al.

(10) Patent No.: US 8,380,279 B2
(45) Date of Patent: Feb. 19, 2013

(54) INTRALUMINAL MULTIFUNCTIONAL SENSOR SYSTEM AND METHOD OF USE

(75) Inventors: Audrius Brazdeikis, Missouri City, TX (US); Ching-Wu Chu, Houston, TX (US)

(73) Assignee: The University of Houston System, Houston, TX (US)

( * ) Notice: Subject to any disclaimer, the term of this patent is extended or adjusted under 35 U.S.C. 154(b) by 1018 days.

(21) Appl. No.: 11/918,145

(22) PCT Filed: May 11, 2006

(86) PCT No.: PCT/US2006/018128
§ 371 (c)(1),
(2), (4) Date: Jan. 30, 2009

(87) PCT Pub. No.: WO2006/122202
PCT Pub. Date: Nov. 16, 2006

(65) Prior Publication Data
US 2009/0177074 A1    Jul. 9, 2009

Related U.S. Application Data

(60) Provisional application No. 60/679,940, filed on May 11, 2005.

(51) Int. Cl.
*A61B 5/05* (2006.01)
*A61B 5/04* (2006.01)
*G01R 33/02* (2006.01)
(52) U.S. Cl. .................. 600/409; 600/374; 324/244
(58) Field of Classification Search .................. None
See application file for complete search history.

(56) References Cited

U.S. PATENT DOCUMENTS

| | | | |
|---|---|---|---|
| 3,449,662 | A | 6/1969 | Wood |
| 4,324,255 | A | 4/1982 | Barach et al. |
| 4,535,381 | A | 8/1985 | Rayburn |
| 4,672,972 | A | 6/1987 | Berke |
| 5,293,119 | A | 3/1994 | Podney |
| 5,384,109 | A | 1/1995 | Klaveness et al. |
| 5,414,356 | A | 5/1995 | Yoshimura et al. |
| 5,565,778 | A | 10/1996 | Brey et al. |
| 5,585,723 | A | 12/1996 | Withers et al. |
| 5,699,801 | A | 12/1997 | Atalar et al. |

(Continued)

FOREIGN PATENT DOCUMENTS

| | | |
|---|---|---|
| DE | 4218635 | 12/1993 |
| EP | 1251361 | 10/2002 |

(Continued)

OTHER PUBLICATIONS

Wosik J et al: "A novel planar design of 200 MHz superconducting array" Proceedings of the International Society for Magnetic Resonance in Medicine, 11th Scientific Meeting and Exhibition, Toronto, Ontario, Canada, Jul. 10-16, 2003, p. 2373, XP002348446.

(Continued)

*Primary Examiner* — Long V. Le
*Assistant Examiner* — Angela M Hoffa
(74) *Attorney, Agent, or Firm* — Robert W Strozier

(57) ABSTRACT

An intraluminal sensor designs for multifunctional characterization of injured, stunned, infarcted myocardium, atherosclerotic plagues and tumors are disclosed. Various embodiments of the present invention comprise the sensor tips for a catheter. The tips comprises differential sensor arrangements, and use built-in electromagnet assemblies for a single or multiple axis sensing of various parameters of local magnetic field.

10 Claims, 7 Drawing Sheets

U.S. PATENT DOCUMENTS

| | | | | |
|---|---|---|---|---|
| 5,978,694 | A * | 11/1999 | Rapoport | 600/407 |
| 6,121,776 | A | 9/2000 | Marek | |
| 6,171,240 | B1 | 1/2001 | Young et al. | |
| 6,177,797 | B1 | 1/2001 | Srinivasan | |
| 6,219,572 | B1 | 4/2001 | Young | |
| 6,252,403 | B1 | 6/2001 | Alsop | |
| 6,253,770 | B1 * | 7/2001 | Acker et al. | 128/899 |
| 6,400,981 | B1 * | 6/2002 | Govari | 600/509 |
| 6,615,071 | B1 | 9/2003 | Casscells, III et al. | |
| 6,633,161 | B1 | 10/2003 | Vaughan, Jr. | |
| 6,727,700 | B2 | 4/2004 | Marek | |
| 6,798,204 | B2 | 9/2004 | Seeber et al. | |
| 6,842,003 | B2 | 1/2005 | Heid et al. | |
| 6,950,063 | B2 | 9/2005 | Nesteruk et al. | |
| 6,971,391 | B1 * | 12/2005 | Wang et al. | 128/846 |
| 7,268,664 | B2 | 9/2007 | Tanaka et al. | |
| 7,496,397 | B2 * | 2/2009 | Smith | 600/423 |
| 7,742,799 | B2 * | 6/2010 | Mueller et al. | 600/410 |
| 7,996,055 | B2 * | 8/2011 | Hauck et al. | 600/374 |
| 8,116,846 | B2 * | 2/2012 | Smith | 600/423 |
| 8,212,554 | B2 * | 7/2012 | Brazdeikis et al. | 324/244 |
| 2002/0067167 | A1 | 6/2002 | Romo et al. | |
| 2002/0165448 | A1 | 11/2002 | Ben-Haim et al. | |
| 2003/0028101 | A1 | 2/2003 | Weisskoff et al. | |
| 2003/0095923 | A1 | 5/2003 | Ohkawa | |
| 2003/0187347 | A1 * | 10/2003 | Nevo et al. | 600/424 |
| 2004/0130323 | A1 | 7/2004 | Oohashi et al. | |
| 2004/0138558 | A1 | 7/2004 | Dunki-Jacobs et al. | |
| 2004/0225213 | A1 * | 11/2004 | Wang et al. | 600/421 |
| 2005/0059852 | A1 | 3/2005 | Rioux et al. | |
| 2005/0171427 | A1 * | 8/2005 | Nevo et al. | 600/424 |
| 2005/0251032 | A1 * | 11/2005 | Smith | 600/433 |
| 2007/0013377 | A1 | 1/2007 | Wosik et al. | |
| 2008/0278166 | A1 | 11/2008 | Wosik et al. | |
| 2008/0294042 | A1 * | 11/2008 | Smith | 600/433 |
| 2009/0177074 | A1 | 7/2009 | Brazdeikis et al. | |
| 2009/0201016 | A1 | 8/2009 | Hattersley et al. | |

FOREIGN PATENT DOCUMENTS

| | | |
|---|---|---|
| FR | 2616911 | 12/1988 |
| FR | 2689638 | 8/1993 |
| GB | 2109112 | 5/1983 |
| JP | 01-151438 | 9/1989 |
| JP | 02-084933 | 6/1990 |
| WO | WO 9729684 A1 * | 8/1997 |

OTHER PUBLICATIONS

Chow MS et al: "A two-channel HTS thin-film phased array coil for low field MRI" Proceedings of the International Society for Magnetic Resonance in Medicine, 11th Scientific Meeting and Exhibition, Toronto, Ontario, Canada, Jul. 10-16, 2003, p. 2372, XP002348447.

Malagoli A et al: "Radiofrequency response of Ag-sheathed $(Bi,Pb)_2Sr_2Ca_2Cu_3O_{10+x}$ superconducting tapes" Physica C, North-Holland Publishing, Amsterdam, NL, vol. 378-381, Oct. 2002, pp. 1087-1090, XP004383056, ISSN: 0921-4534.

Bock N A et al: "Multiple-mouse MRI" Magnetic Resonance in Medicine, Academic Press, Duluth, MN, US, vol. 49, No. 1, Jan. 2003, pp. 158-167, XP002281379, ISSN: 0740-3194.

International Search Report for PCT/US2006/018129, Sep. 26, 2006.
International Search Report for PCT/US2006/018128, Sep. 27, 2006.
International Search Report for PCT/US2006/018321, Jan. 26, 2007.
International Search Report for PCT/US2005/001813, Oct. 26, 2005.

* cited by examiner

INTRALUMINAL MULTIFUNCTIONAL SENSOR SYSTEM AND METHOD OF USE

RELATED APPLICATIONS

This application claims priority to priority to PCT Patent Application Ser. No. PCT/US06/18128, filed 11 May 2006 (May 11, 2006); WO06/122202; PD: 16 Nov. 2006 (Nov. 16, 2006), which claims priority to U.S. Provisional Patent Application Ser. No. 60/679,940, filed 11 May 2005 (May 11, 2005 or May 5, 2005).

BACKGROUND OF THE INVENTION

1. Field of the Invention

The present invention relates to an intraluminal sensor design for multifunctional characterization of injured, stunned, infarcted myocardium, atherosclerotic plagues and tumors.

More particularly, the present invention relates to an intraluminal sensor design for multifunctional characterization of injured, stunned, infarcted myocardium, atherosclerotic plagues and tumors, where the sensor includes

2. Description of the Related Art

U.S. Pat. No. 5,735,279 to Klavenes, et al. discloses the use of a magneto sensor magnetometer to detect magnetic changes in vivo. U.S. Pat. No. 6,027,946 to Weiteschies, et al. discloses the use of a magneto sensor detector to measure the spacial distribution of relaxing magnetic markers in vivo. U.S. Pat. No. 5,594,849 to Kuc, et al. discloses the use of magneto sensor magnetometers for measuring magnetic field intensity. U.S. Pat. No. 6,123,902 to Koch, et al. discloses the use of a magneto sensor detector to detect small amounts of bound analytes in a solution. U.S. Pat. No. 6,048,515 to Kresse, et al. discloses the use of nanoparticles comprising an iron containing core and a targeting polymer coating to determine the biological behavior of the nanoparticles.

However, there is still a need in the art for intraluminal sensors for multifunctional characterization of injured, stunned, infarcted myocardium, atherosclerotic plagues and tumors.

SUMMARY OF THE INVENTION

The present invention provides an intraluminal sensor design for multifunctional characterization of injured, stunned, infarcted myocardium, atherosclerotic plagues and tumors. The intraluminal sensor includes a sensing element attached to a distal end of a catheter and includes differential sensing element arrangements. The sensors includes a built-in electromagnet assembly. The sensing elements can be disposed along a single axis or plane or along multiple axes or planes. The sensor is adapted to sense various parameters of a local magnetic field or a magnetic field distribution of an area of interest adjacent an artery, vein or other bodily structure subject to catheter deployment. The sensor of this invention may also include auxiliary sensors or groups of auxiliary sensors simultaneously or sequentially for measuring local physiological parameters in the vicinity of the sensor such as temperature, pressure, pH, chemical composition, and blood assay.

The present invention provides a magnetic detection system including a catheter having a sensor of this invention mounted on its distal end. The sensor is adapted to measure magnetic fields and/or magnetic field distribution associated with locations in an area of interest in an animal, including an human, body. The area of interest is generally accessible via a artery or a vein or other duct or channel that can accommodate a catheter.

The present invention provides a magnetic detection system including a catheter having a sensor of this invention and a ultrasonic transmitter mounted on its distal. The sensor is adapted to measure magnetic fields and/or magnetic field distribution associated with locations in an area of interest in an animal, including an human, body. The ultrasonic transmitter, which can be a dual beam ultrasonic transmitter, is adapted to introduce a mechanical vibration to locations with in the area of interest.

The present invention provides a magnetic detection system including a catheter having a magneto sensor, a ultrasonic transmitter, a coil mounted on its distal and a magnetically active agent introduction conduit having an orifice disposed at or near the distal end of the catheter. The sensor is adapted to measure magnetic fields and/or magnetic field distribution associated with locations in an area of interest in an animal, including an human, body. The ultrasonic transmitter, which can be a dual beam ultrasonic transmitter, is adapted to introduce a mechanical vibration to the locations with in the area of interest. The coil is adapted to introduce a modulation to the locations with in the area of interest. The conduit is designed to introduce a magnetically active agent into the area of interest.

The present invention also provides a method for measuring magnetic fields, magnetic field distributions and/or changes therein, where the method includes inserting a catheter of this invention into an artery, vein or other suitable structure in an animal, including an human and positioning a distal end of the catheter adjacent an area of interest of the animal. The method also includes the step of measuring a magnetic field distribution of the area of interest. The method may also include the step of making a series of magnetic field distribution measurements as the catheter is moved within the artery or vein to acquire a distribution along the artery or vein. The method also includes the step of administering a magnetically active agent to the animal before and/or after measuring the magnetic field distribution. The method may also include the step of making a second series of magnetic field distribution measurements as the catheter is moved within the artery or vein to acquire a distribution along the artery or vein after administration of the magnetically active agent. The method can also include applying a controlled external magnetic field to the area of interest to produce a controlled modulation of any magnetically active agent within loci within the area of interest. The method can also include applying an ultrasonic beam to the area of interest to induce mechanical vibrations of magnetically active agents accumulated in loci within the area of interest. The method may includes the step of comparing different distribution or field data to obtain data before and after administration, modulation or mechanical vibration. The method also includes analyzing the data to identify locations within the area of interest that evidence an accumulation of magnetically active agents. The analyzing step can also use imaging data such as ultrasonic data to register the magnetic data, where registration means that the magnetic data is made to conform to physical locations within the area of interest. The method can also include the step of measuring a physical and/or chemical property in, near or surrounding the area of interest. The method of the present invention may be employed for various medical diagnostic purposes, such as locating vulnerable plaque in a patient's body.

BRIEF DESCRIPTION OF THE DRAWINGS

The invention can be better understood with reference to the following detailed description together with the appended illustrative drawings in which like elements are numbered the same.

DETAILED DESCRIPTION OF THE INVENTION

The inventors have found that new magneto sensor apparatuses for attachment to a distal end of a catheter can be construction including a plurality of sensing elements or arrays thereof, where the sensing elements include magnetic or magneto sensors, temperature sensors, pH sensors, chemical sensors, ion specific sensors, or a combination thereof. The apparatus include a built-in electromagnet for the application of external magnetic field to augment a measured magnetic field in an area of interest proximate the sensor apparatus via catheter insertion into an animal, including an human.

Catheter Sensor Tips of this Invention

Figure 1A:
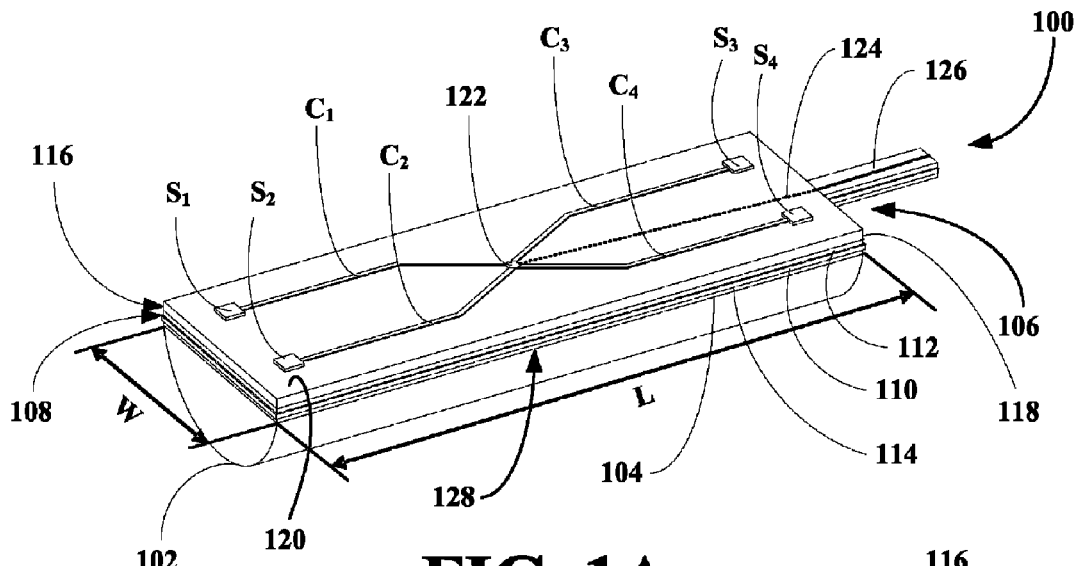
FIG. 1A-C depict an isometric view, a side view and a top view of an embodiment of an intraluminal sensor of the present invention.
Figure 1B:
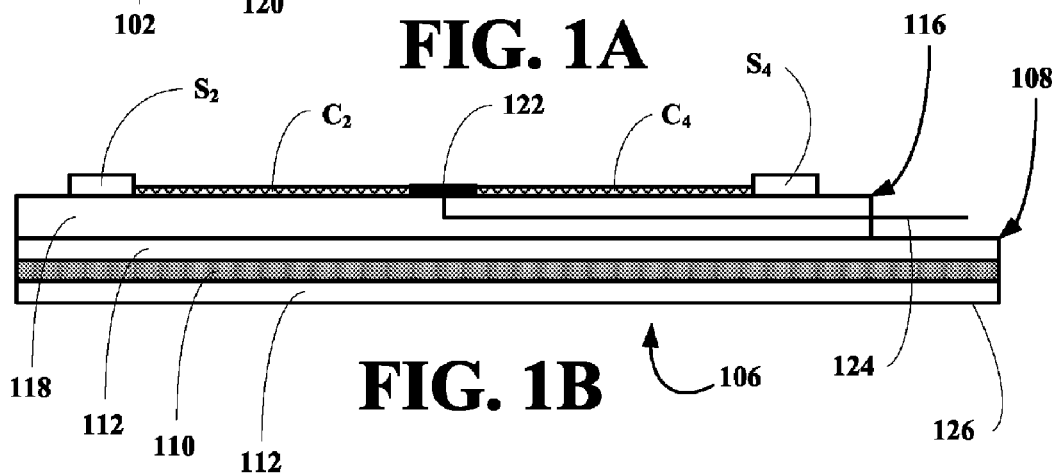
Figure 1C:
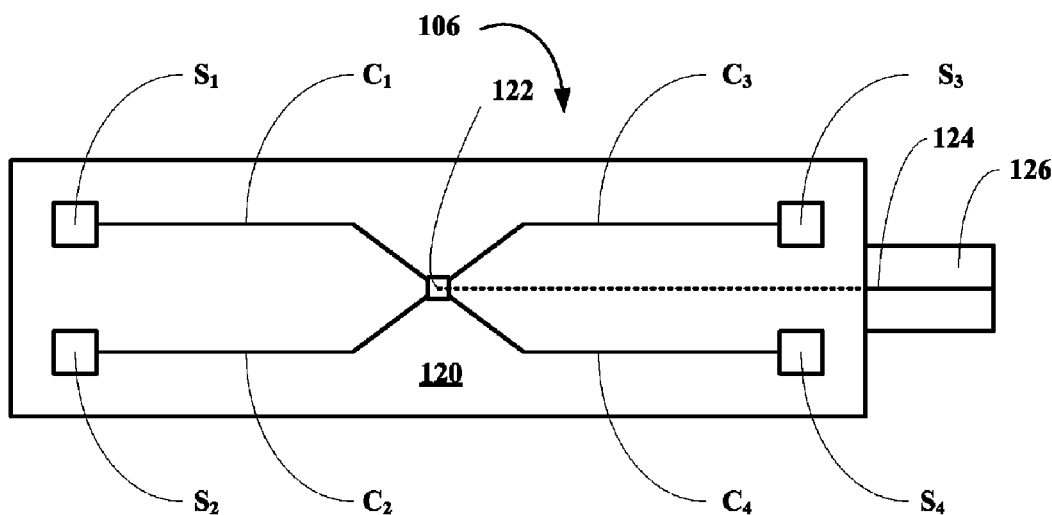

Referring now to FIGS. 1A-C, three views of an embodiment of an intravascular magneto sensor apparatus of the present invention, generally 100, are shown, where the apparatus is adapted to be attached to, affixed to or connected to a distal ent of a catheter which can be inserted into a body and directed to adjacent an area of interest accessible from an artery, vein or other bodily structure amenable to catheter insertion. Looking at FIG. 1A, the apparatus 100 includes a hemi-spherically shaped base 102. On the flat surface 104 of the base 102 is disposed a multi-layered sensor assembly 106. The assembly 106 includes an electromagnet (EM) construct 108 including an electromagnetic (EM) layer 110 sandwiched between two support and protective layers 112 and 114. The assembly 106 also includes a sensor construct 116 disposed on top of the EM construct 108. The sensor construct 116 includes a sensor support layer 118 and a four magneto-sensing elements $S_1$, $S_2$, $S_3$ and $S_4$ disposed on a top surface 120 of the layer 118. The elements $S_1$, $S_2$, $S_3$ and $S_4$ are connected to a contact 122 via conducting elements $C_1$, $C_2$, $C_3$ and $C_4$, respectively. The contact 122 is in electrical communication with a sensor cable 124. The assembly 106 also includes a tab 126 adapted to be inserted into a catheter attaching the assembly 106 to the catheter and to connect the EM layer 110 and the sensor cable 122 to electrical conduits extending through the catheter to a power source for supply power to the EM layer 110 and an receiver for receiving sensing data from the sensors $S_1$, $S_2$, $S_3$ and $S_4$. A head portion 128 of the assembly 106 has a length L and a width W.

Figure 2A:
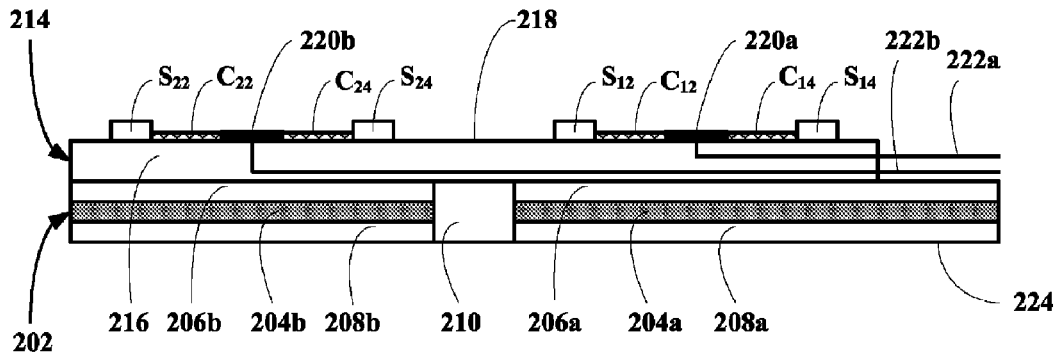
FIG. 2A-C depict a side view and a top view of an embodiment of an intraluminal sensor of the present invention and a view of the two field EM layer.
Figure 2B:
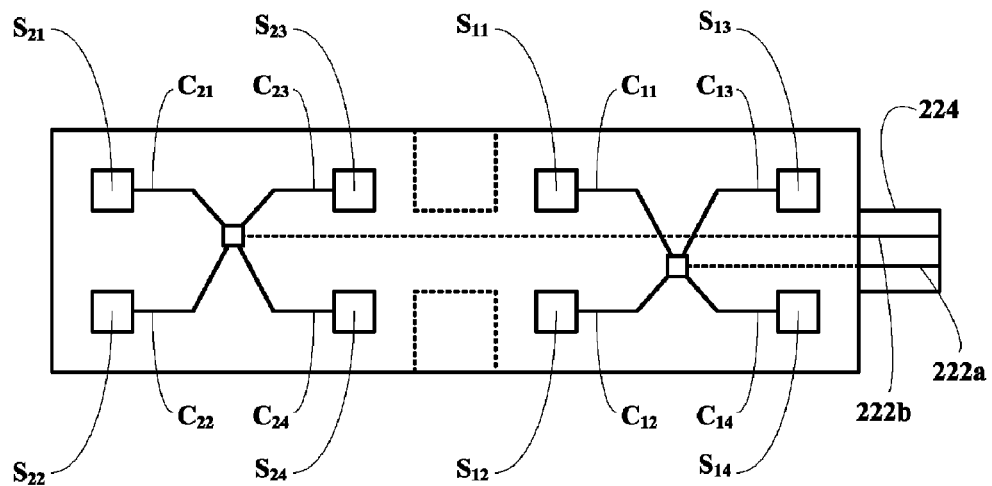
Figure 2C:
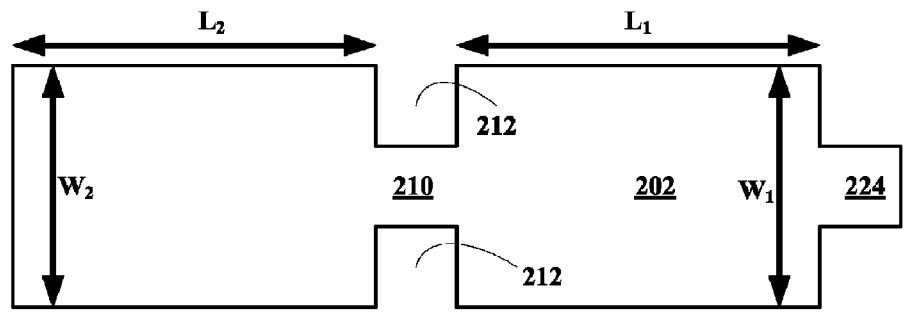

Referring now to FIGS. 2A-C, three views of another embodiment of a multi-layered sensor assembly, generally 200, of an intravascular magneto sensor apparatus of the present invention are shown, which is split-electromagnet design (EM-1 and EM-2). Looking at FIG. 2A, the assembly 200 includes an electromagnet (EM) construct 202 including a first and second electromagnetic (EM) layers 204a and 204b sandwiched between two support and protective layers 206a & b and 208a & b. The EM construct 202 also includes a connecting member 210 forming notches 212 in the construct 202. The assembly 206 also includes a sensor construct 214 disposed on top of the EM construct 202. The sensor construct 214 includes a sensor support layer 216 and a eight magneto-sensing elements $S_{11}$, $S_{12}$, $S_{13}$ and $S_{14}$ and $S_{21}$, $S_{22}$, $S_{23}$ and $S_{24}$ disposed on a top surface 218 of the layer 216 so that the elements $S_{11}$, $S_{12}$, $S_{13}$ and $S_{14}$ are disposed above the EM layer 204a, while the elements $S_{21}$, $S_{22}$, $S_{23}$ and $S_{24}$ are disposed above the EM layer 204b. The elements $S_{11}$, $S_{12}$, $S_{13}$ and $S_{14}$ are connected to a contact 220a via conducting elements $C_{11}$, $C_{12}$, $C_{13}$ and $C_{14}$, respectively; while the $S_{21}$, $S_{22}$, $S_{23}$ and $S_{24}$ are connected to a contact 220b via conducting elements $C_{21}$, $C_{22}$, $C_{23}$ and $C_{24}$, respectively. The contacts 220a & b are in electrical communication with sensor cables 222a & b, respectively. The assembly 206 also includes a tab 224 adapted to be inserted into a catheter attaching the assembly 206 to the catheter and to connect the EM layers 204a & b and the sensor cables 222a & b to electrical conduits extending through the catheter to a power source for supply power to the EM layers 204a & b and an receiver for receiving sensing data from the sensors $S_1$, $S_2$, $S_3$ and $S_4$. The EM layer 204a & b have length $L_1$ and $L_2$, respectively, and width $W_1$ and $W_2$, respectively, where the lengths can be the same or different and the widths can be the same of different. Moreover, the material comprising in the EM layer can be the same or different. By changing the EM layer material, its length and width, each sensor array can sense magnetic field distribution in the presence of different applied magnetic field.

Figure 3A:
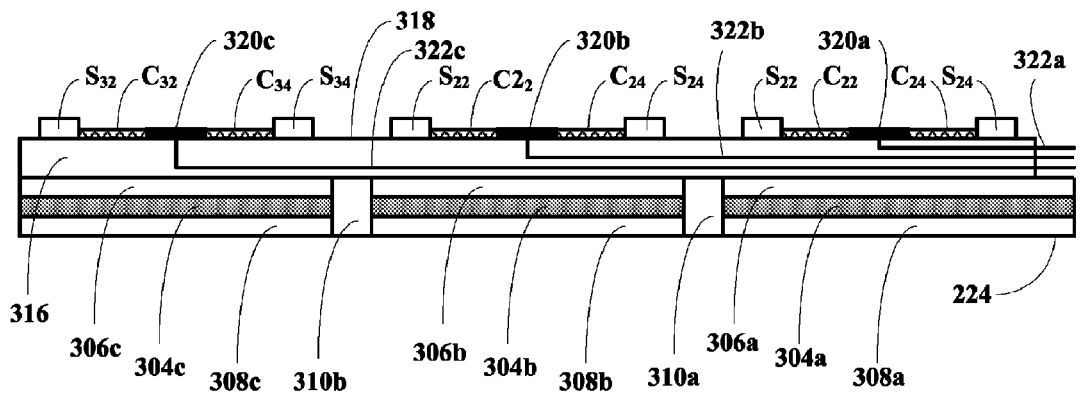
FIG. 3A-C depict a side view and a top view of an embodiment of an intraluminal sensor of the present invention and a view of the two field EM layer.
Figure 3B:
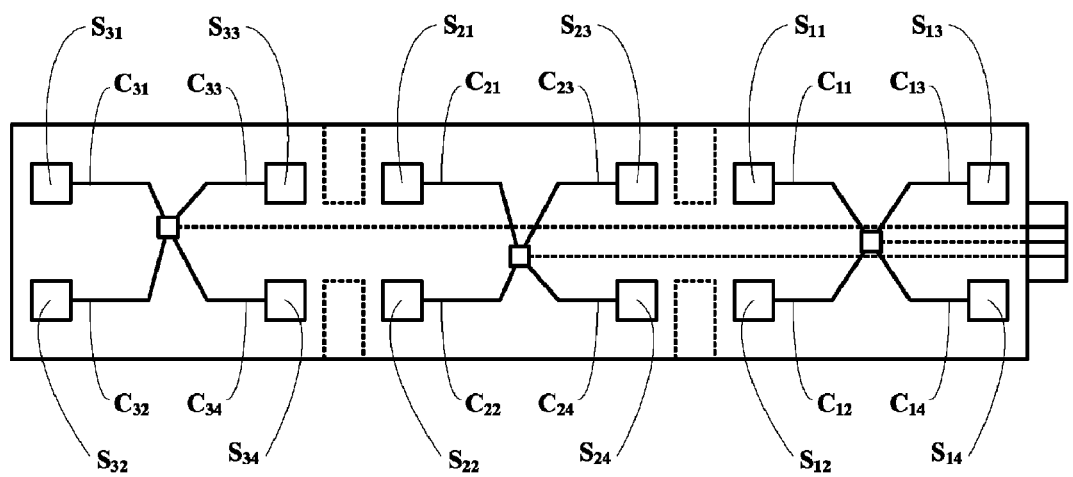
Figure 3C:
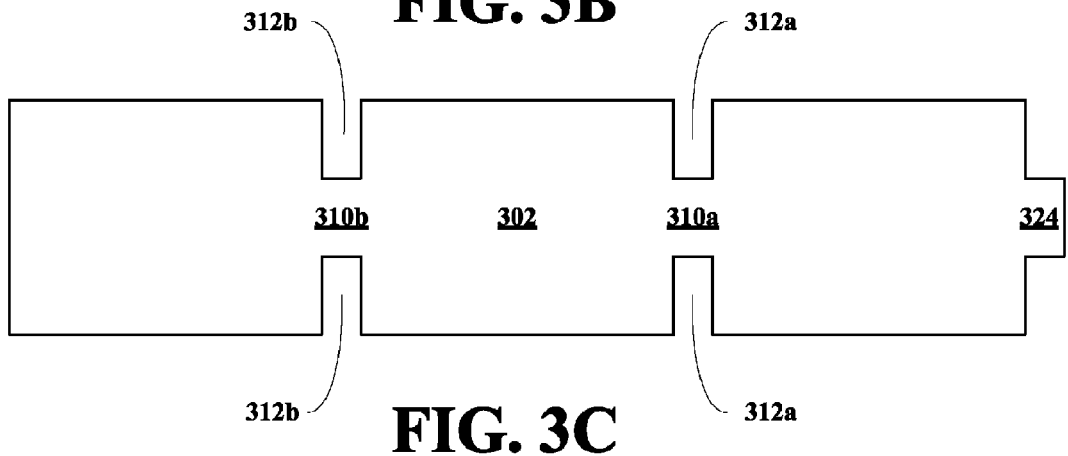

Referring now to FIGS. 3A-C, three views of another embodiment of a multi-layered sensor assembly, generally 300, of an intravascular magneto sensor apparatus of the present invention are shown, which is a triple split-electromagnet design (EM-1, EM-2 and EM-3). Looking at FIG. 3A, the assembly 300 includes an electromagnet (EM) construct 302 including a first and second electromagnetic (EM) layers 304a-c sandwiched between two support and protective layers 306a-c and 308a-c. The EM construct 302 also includes a connecting member 310a-b forming notches 312a-b in the construct 302. The assembly 306 also includes a sensor construct 314 disposed on top of the EM construct 302. The sensor construct 314 includes a sensor support layer 316 and a eight magneto-sensing elements $S_{11}$, $S_{12}$, $S_{13}$ and $S_{14}$ and $S_{21}$, $S_{22}$, $S_{23}$ and $S_{24}$ and $S_{31}$, $S_{32}$, $S_{33}$ and $S_{34}$ disposed on a top surface 318 of the layer 316 so that the elements $S_{11}$, $S_{12}$, $S_{13}$ and $S_{14}$ are disposed above the EM layer 304a; the elements $S_{21}$, $S_{22}$, $S_{23}$ and $S_{24}$ are disposed above the EM layer 304b; while the elements $S_{31}$, $S_{32}$, $S_{33}$ and $S_{34}$ are disposed above the EM layer 304c. The elements $S_{11}$, $S_{12}$, $S_{13}$ and $S_{14}$ are connected to a contact 320a via conducting elements $C_{11}$, $C_{12}$, $C_{13}$ and $C_{14}$, respectively; the $S_{21}$, $S_{22}$, $S_{23}$ and $S_{24}$ are connected to a contact 320b via conducting elements $C_{21}$, $C_{22}$, $C_{23}$ and $C_{24}$, respectively; while the $S_{31}$, $S_{32}$, $S_{33}$ and $S_{34}$ are connected to a contact 320c via conducting elements $C_{31}$, $C_{32}$, $C_{33}$ and $C_{34}$, respectively. The contacts 320a-c are in electrical communication with sensor cables 322a-c, respectively. The assembly 306 also includes a tab 324 adapted to be inserted into a catheter attaching the assembly 306 to the catheter and to connect the EM layers 304a-c and the sensor cables 322a-c to electrical conduits extending through the catheter to a power source for supply power to the EM layers 304a-c and an receiver for receiving sensing data from the sensors $S_1$, $S_2$, $S_3$ and $S_4$. The EM layer 304a-c have length $L_1$, $L_2$ and $L_3$, respectively, and width $W_1$, $W_2$ and $W_3$, respectively, where the lengths can be the same or different and the widths can be the same of different. Moreover, the material comprising in the EM layer can be the same or different. By changing the EM layer material, its length and width, each sensor array can sense magnetic field distribution in the presence of different applied magnetic field.

These embodiments are directed to an intraluminal multifunction sensor of a planar design with differential sensor arrangement. The planar sensor arrangement or sensing layer comprises microfabricated magnetosensors. An example of the magnetosensor is microfabricated magnetoresistive sensor. The sensors can be based on the giant magnetoresistive (GMR) sensors, colossal magnetoresistive (CMR), extraordinary magnetoresistive (EMR), ballastic magnetoresistive (BMR), or other magnetoresistive sensors or mixtures or combinations thereof. By constructing catheter tips having multiple sensing element arrays covering a fairly long span, the tips can be used to magnetically image a long span of an artery such as the coronary arteries without having to move the catheter along the artery.

Figure 4:
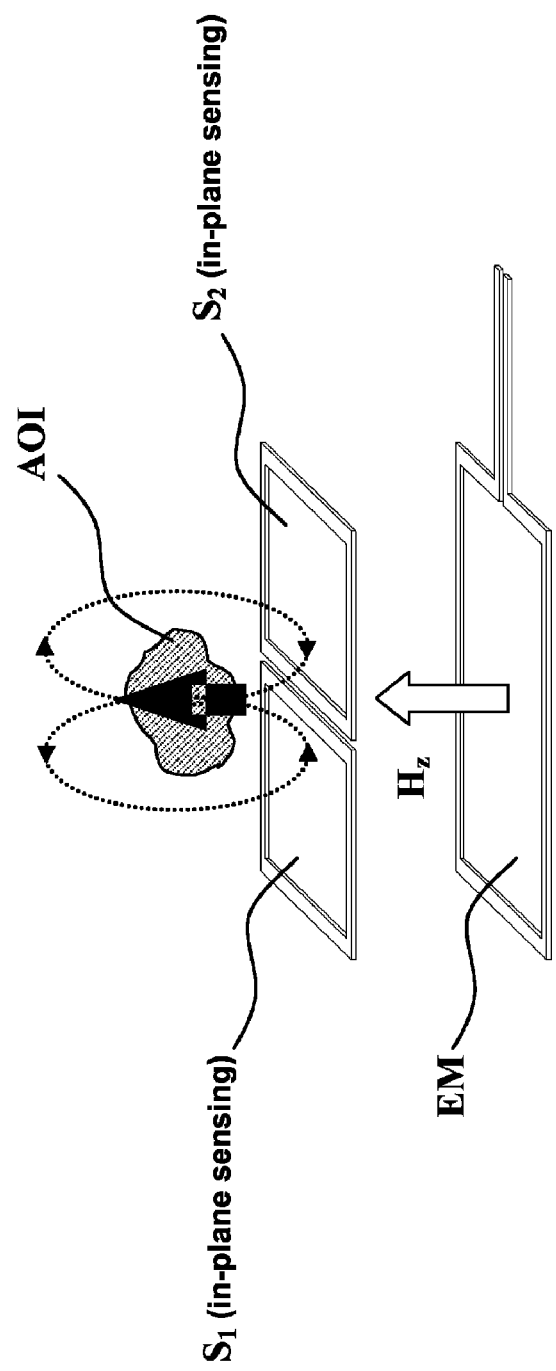
FIG. 4 depicts an isometric view of a diagram of the method of operation of a multi-element sensor of this invention.

Referring now to FIG. 4, the built-in electromagnet (EM) produces an excitation magnetic field $H_z$, typically not exceeding a saturation field of the sensing layer. Individual microfabricated magnetosensors $S_1$-$S_4$ sense field components other than excitation field. The sensed fields are in the plane containing each magnetosensors $S_1$-$S_4$ as shown by circulating field associated with an area of interest AOI. Thus, each magnetosensors $S_1$-$S_4$ senses as slightly different magnetic field associated with the AOI. One can be use differential analysis techniques to gain information about the magnetic field distributions associated with the AOI both before and after the administration of a magnetically active agent to the AOI. The AOI can be a location in an animal, including an human.

Figure 5A:
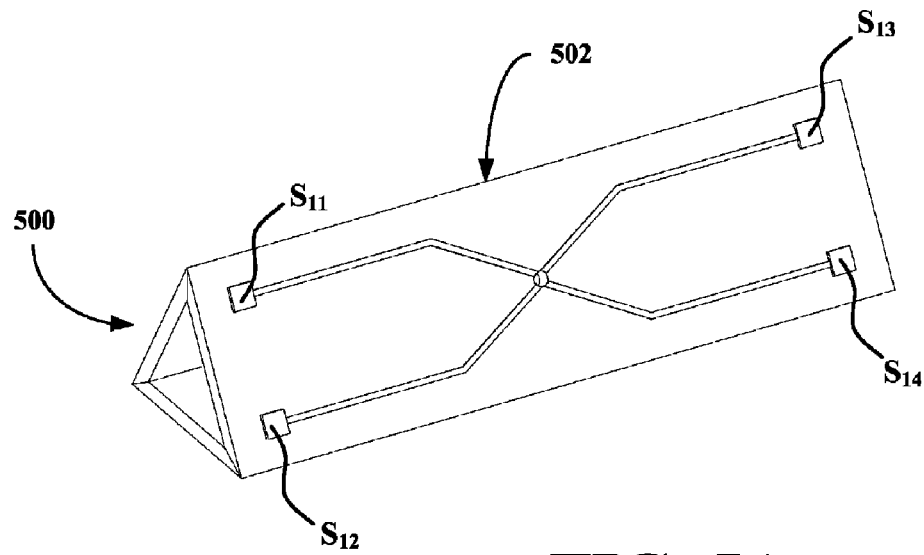
FIG. 5A-B depicts an isometric view and a front view of another embodiment of a multi-element sensor of this invention.
Figure 5B:
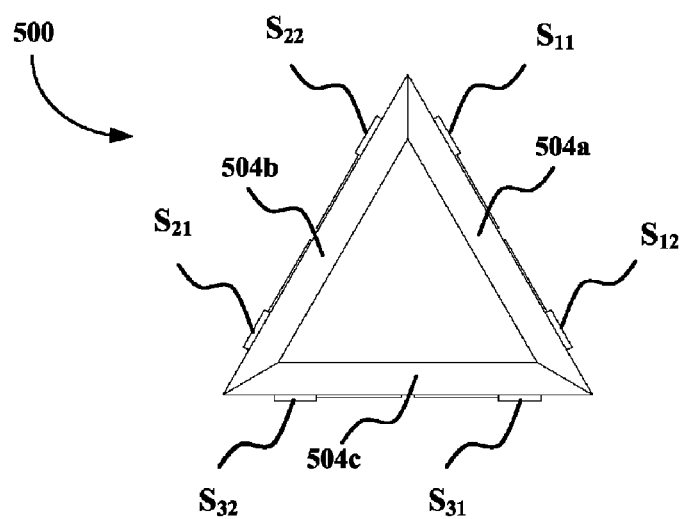

Referring now to FIGS. 5A-B, two views of an embodiment of a 3-axis intravascular magneto sensor apparatus the invention, generally 500, are shown, where the apparatus is adapted to simultaneously sensing along three independent axes. The apparatus 500 includes the same basic structure as the embodiments of FIGS. 1A-C, 2A-C and 3A-C, but the assembly 502 is in the form or a hollow triangular solid. The assembly 502 includes three sides 504a-c. The surface 504a includes four sensing elements $S_{11}$, $S_{12}$, $S_{13}$ and $S_{14}$. The surface 504b includes four sensing elements $S_{21}$, $S_{22}$, $S_{23}$ and $S_{24}$. And, the surface 504c includes four sensing elements $S_{31}$, $S_{32}$, $S_{33}$ and $S_{34}$. This embodiment is directed to an intraluminal multifunction sensor of non-planar design with differential, multiple axis sensor arrangement.

Figure 6:
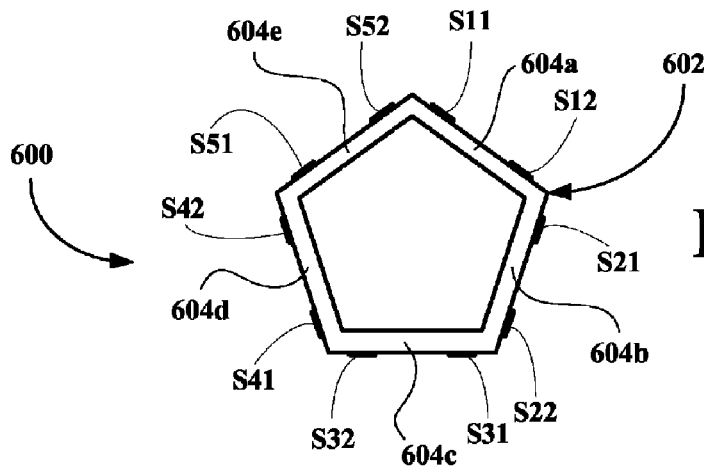
FIG. 6 depicts a front view of another embodiment of a multi-element sensor of this invention.

Referring now to FIG. 6, an embodiment of a 5-axis intravascular magneto sensor apparatus the invention, generally 600, are shown, where the apparatus is adapted to simultaneously sensing along five independent axes. The apparatus 600 includes the same basic structure as the embodiments of FIGS. 1A-C, 2A-C and 3A-C, but the assembly 602 is in the form or a hollow pentagonal solid. The assembly 602 includes five sides 604a-e. The surface 604a includes four sensing elements $S_{11}$, $S_{12}$, $S_{13}$ and $S_{14}$. The surface 604b includes four sensing elements $S_{21}$, $S_{22}$, $S_{23}$ and $S_{24}$. The surface 604c includes four sensing elements $S_{31}$, $S_{32}$, $S_{33}$ and $S_{34}$. The surface 604d includes four sensing elements $S_{41}$, $S_{42}$, $S_{43}$ and $S_{44}$. And, the surface 604e includes four sensing elements $S_{51}$, $S_{52}$, $S_{53}$ and $S_{54}$. This embodiment is directed to an intraluminal multifunction sensor of non-planar design with differential, multiple axis sensor arrangement.

Figure 7:
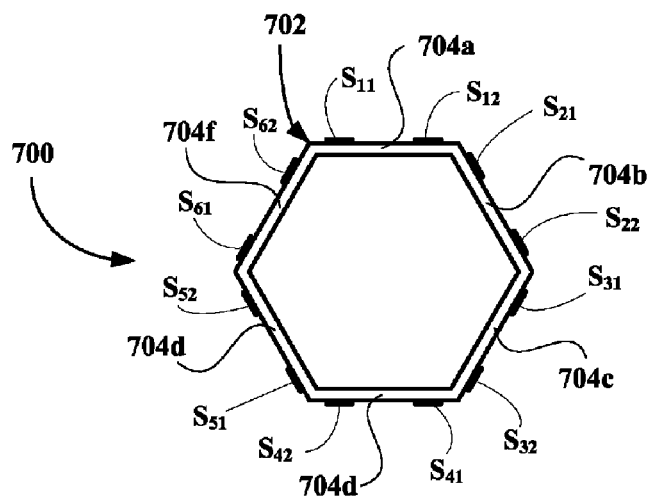
FIG. 7 depicts a front view of another embodiment of a multi-element sensor of this invention.

Referring now to FIG. 7, an embodiment of a 6-axis intravascular magneto sensor apparatus the invention, generally 700, are shown, where the apparatus is adapted to simultaneously sensing along six independent axes. The apparatus 700 includes the same basic structure as the embodiments of FIGS. 1A-C, 2A-C and 3A-C, but the assembly 702 is in the form or a hollow hexagonal solid. The assembly 502 includes six sides 704a-f. The surface 704a includes four sensing elements $S_{11}$, $S_{12}$, $S_{13}$ and $S_{14}$. The surface 704b includes four sensing elements $S_{21}$, $S_{22}$, $S_{23}$ and $S_{24}$. The surface 704c includes four sensing elements $S_{31}$, $S_{32}$, $S_{33}$ and $S_{34}$. The surface 704d includes four sensing elements $S_{41}$, $S_{42}$, $S_{43}$ and $S_{44}$. The surface 704e includes four sensing elements $S_{51}$, $S_{52}$, $S_{53}$ and $S_{54}$. And, the surface 704f includes four sensing elements $S_{61}$, $S_{62}$, $S_{63}$ and $S_{64}$. This embodiment is directed to an intraluminal multifunction sensor of non-planar design with differential, multiple axis sensor arrangement.

Figure 8:
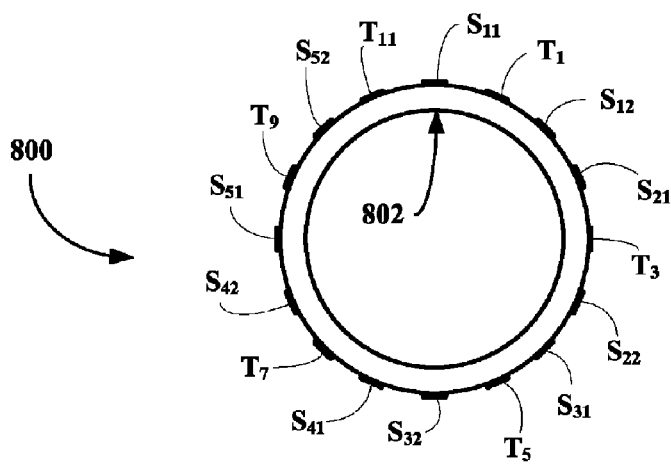
FIG. 8 depicts a front view of another embodiment of a multi-element sensor of this invention.

Referring now to FIG. 8, another embodiment of a cylindrical intravascular magneto sensor apparatus the invention, generally 800, are shown, where the apparatus is adapted to simultaneously sensing along three independent axes. The apparatus 800 includes the same basic structure as the embodiments of FIGS. 1A-C, 2A-C and 3A-C, but the assembly 802 is in the form or a hollow cylindrical solid. The cylinder 802 includes a first set of four sensing elements $S_{11}$, $S_{12}$, $S_{13}$ and $S_{14}$ disposed on the outer surface of the cylinder 802. The cylinder 802 includes a second set of four sensing elements $S_{21}$, $S_{22}$, $S_{23}$ and $S_{24}$. The cylinder 802 includes a third set of four sensing elements $S_{31}$, $S_{32}$, $S_{33}$ and $S_{34}$. The cylinder 802 includes a fourth set of four sensing elements $S_{41}$, $S_{42}$, $S_{43}$ and $S_{44}$. And, the cylinder 802 includes a fifth set of four sensing elements $S_{51}$, $S_{52}$, $S_{53}$ and $S_{54}$. This embodiment is directed to an intraluminal multifunction sensor of non-planar design with differential, multiple axis sensor arrangement. The cylinder 802 also includes five set of auxiliary sensors $T_1$-$T_{11}$, where only the odd sensors are shown.

It should be recognized that the multi-axes embodiments of this invention can be of any regular or irregular polygonal shaped solid. Although planar, triangular, pentagonal, hexagonal and cylindrical were shown, an ordinary artisan would clearly recognize that other polygonal solids such as square, rectangular, heptagonal, octagonal, nonagonal, decagonal, etc. can be used as well.

Figure 9:
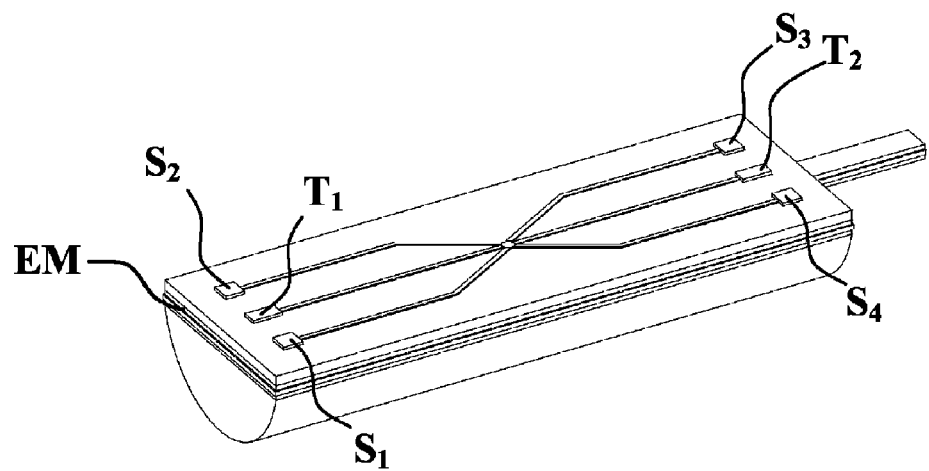
FIG. 9 depicts an isometric view of another embodiment of a multi-element sensor of this invention.

Referring now to FIG. 9, another embodiment of a intravascular magneto sensor apparatus the invention of FIG. 1A, including auxiliary sensing elements $T_1$ and $T_2$ for simultaneous or subsequent differential measurements locally of physiological parameters such as a temperature sensor, a blood pressure sensor, an pH sensor, a chemical composition sensor, an ion specific sensor, and a blood assay sensor, or a combination thereof.

Figure 10:
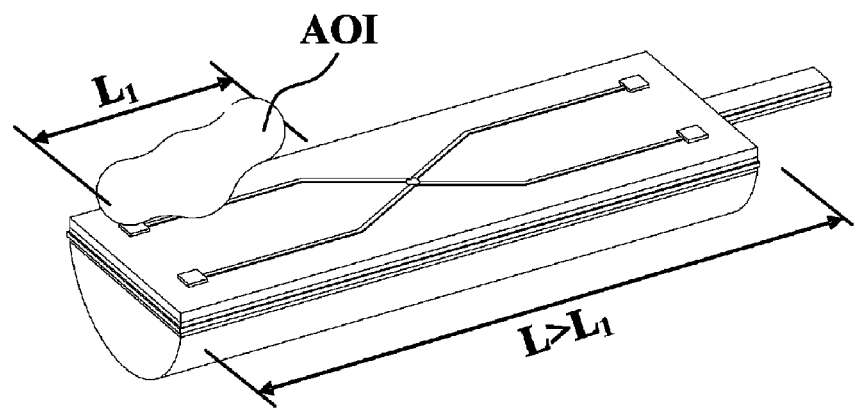
FIG. 10 depicts an isometric view of another embodiment of a multi-element sensor of this invention.

A first method embodiment of the present invention is shown in FIG. 10. This embodiment is directed toward a method for identifying loci in a target body that accumulates magnetic substances. The differential sensor base L is chosen to be larger than an area of interest (AOI) to be detected. The differential sensor base L is typically chosen to be long enough to electronically subtract background noise locally present due to environment or from surrounding electrically active tissues. Examples of areas of local characterization may be injured, stunned, and infarcted myocardium, atherosclerotic plaque, benign and tumor lesions.

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

We claim:

1. An intraluminal sensor apparatus for multifunctional characterization of injured, stunned, infarcted myocardium, atherosclerotic plaques and tumors comprising:
   a catheter including a sensor assembly disposed on a distal end thereof, where the assembly comprises:
   an electromagnet construct and
   a sensor construct,
      where the electromagnet construct comprises an electromagnetic layer interposed between two support and protective layers and
      where the sensor construct comprises a sensor substrate layer disposed on one of the two support and protective layers of the electromagnet construct,
      where the sensor substrate layer includes a plurality of sensing elements disposed thereon and configured to measure local magnetic field distribution.

2. The apparatus of claim 1, wherein the sensing elements are in a differential sensing element arrangement along a single axis, a plane or along multiple axes or planes.

3. The apparatus of claim 1, wherein the apparatus has a planar design and the sensor assembly senses in a single direction.

4. The apparatus of claim 1, wherein the apparatus has a non-planar design and the sensor assembly senses in a single direction or multiple directions.

5. The apparatus of claim 1, wherein the sensor assembly further comprises one or a plurality of auxiliary sensors.

6. The apparatus of claim 1, wherein the electromagnetic layer comprises a plurality of electromagnets, each electromagnet associated with an array of the plurality of sensing elements.

7. An intraluminal sensor apparatus for multifunctional characterization of injured, stunned, infarcted myocardium, atherosclerotic plaques and tumors comprising:
   a catheter including a sensor assembly disposed on its distal end, where the assembly comprises:
      an electromagnet construct including:
         an electromagnetic layer interposed between two support and protective layers, and
      a sensor construct including:
         a sensor substrate layer disposed on one of the two support and protective layers of the electromagnet construct, where the sensor substrate layer includes a plurality of sensing elements disposed thereon,
   where the sensing elements comprise a first group of sensing elements disposed in a differential sensing element arrangement along a single axis, a plane or along multiple axes or planes and a second group of sensing elements configured to simultaneously or subsequently measure local physiological parameters comprising at least one of temperature, pressure, pH, chemical composition, and blood assay, where the first group of sensing elements is configured to measure local magnetic field distribution.

8. The apparatus of claim 7, wherein the apparatus has a planar design and the sensor assembly senses in a single direction.

9. The apparatus of claim 7, wherein the apparatus has a non-planar design and the sensor assembly senses in a single direction or multiple directions.

10. The apparatus of claim 7, wherein the electromagnetic layer comprises a plurality of electromagnets, each electromagnet associated with an array of the plurality of sensing elements.

* * * * *